(12) United States Patent
Visser et al.

(10) Patent No.: US 8,427,527 B2
(45) Date of Patent: Apr. 23, 2013

(54) AUTOSTEREOSCOPIC DISPLAY

(75) Inventors: Hugo Visser, Eindhoven (NL); Ivan Salgo, Pelham, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1309 days.

(21) Appl. No.: 11/816,279

(22) PCT Filed: Feb. 10, 2006

(86) PCT No.: PCT/IB2006/050444
§ 371 (c)(1),
(2), (4) Date: May 19, 2008

(87) PCT Pub. No.: WO2006/087663
PCT Pub. Date: Aug. 24, 2006

(65) Prior Publication Data
US 2008/0218589 A1    Sep. 11, 2008

(51) Int. Cl.
*H04N 13/04*    (2006.01)
(52) U.S. Cl.
USPC ............... 348/51; 348/42; 600/407; 600/437
(58) Field of Classification Search ............... 348/42, 348/51, 59
See application file for complete search history.

(56) References Cited

U.S. PATENT DOCUMENTS

| | | | |
|---|---|---|---|
| 5,175,616 A | 12/1992 | Milgram | |
| 5,740,802 A | 4/1998 | Nafis | |
| 6,019,725 A | 2/2000 | Vesely | |
| 6,246,898 B1 | 6/2001 | Vesely | |
| 6,744,848 B2* | 6/2004 | Stanton et al. | 378/55 |
| 7,643,025 B2* | 1/2010 | Lange | 345/419 |
| 2001/0016684 A1 | 8/2001 | Shahidi | |
| 2002/0049375 A1* | 4/2002 | Strommer et al. | 600/407 |
| 2002/0126202 A1* | 9/2002 | Wood et al. | 348/59 |
| 2005/0137477 A1* | 6/2005 | Kockro | 600/437 |

FOREIGN PATENT DOCUMENTS

| | | |
|---|---|---|
| EP | 0641132 A1 | 3/1995 |
| EP | 0791847 A1 | 8/1997 |
| EP | 0817123 A1 | 1/1998 |
| WO | 03013153 A1 | 2/2003 |
| WO | 03034705 A2 | 4/2003 |
| WO | 2004084737 A1 | 10/2004 |

\* cited by examiner

*Primary Examiner* — Yves Dalencourt

(57) ABSTRACT

An autostereoscopic display 101, which provides a depth perception by providing a viewer's left and right eyes (104a, 104b) with two slightly different perspectives of an image to be displayed, is provided for ultrasound guided interventions with a surgical instrument (103). The surgeon watches displayed ultrasound data (102), rendered for at least two views. The plane at which those views (L, R) intersect is adjusted to correspond exactly with the tracked three-dimensional position within a displayed scene of the surgical instrument (103), which position can be extracted from the three-dimensional ultrasound data by means of, for example, 3D object recognition. Thus, the point of reconstruction of the image presented to the viewer can be dynamically adjusted to correspond with the position of the surgical instrument on which the surgeon's eyes are presumed to be focused.

13 Claims, 4 Drawing Sheets

//+# AUTOSTEREOSCOPIC DISPLAY

FIELD OF THE INVENTION

This invention relates generally to an autostereoscopic display system and, more particularly, to an autostereoscopic display system for use in medical imaging during image guided interventions.

BACKGROUND OF THE INVENTION

Autostereoscopic image display systems are known in various forms of implementation, and are aimed at the recreation of the two different perspectives of a three-dimensional view or image as perceived by two human eyes without the need for viewing aids to be worn by the observer. A viewpoint tracker is used to dynamically align the point of recreation with the viewpoint or observer position, as described in, for example International Patent Application No. WO03/013153. The two different perspectives of a three-dimensional view, also referred to as a stereoscopic pair of images, allow the brain to assess the distance to various objects in a scene and to provide for three-dimensional view impression.

During a medical intervention, such as ultrasound-guided interventions, a surgeon would be watching three-dimensional ultrasound data, rendered for at least two views. It is advantageous to align the above-mentioned point of recreation, i.e. the plane where the two (or more) views intersect, with the plane on which the surgeon's eyes are focused. During a medical intervention, this will tend to be the instrument being manipulated.

SUMMARY OF THE INVENTION

It is therefore an object of the present invention to provide an autostereoscopic display system in which the plane in which a stereoscopic pair of images intersect to define the point of recreation of a displayed image is dynamically aligned to correspond with the location of an instrument being manipulated in relation to the subject being imaged. In accordance with the present invention, there is provided an autostereoscopic display system comprising means for presenting first and second images to a viewer's left and right eyes respectively, said first and second images comprising first and second perspectives of a three-dimensional scene to be displayed, said first and second images intersecting at a point of recreation on a plane of said three dimensional scene, the system further comprising tracking means for determining the three-dimensional position within said three-dimensional scene of a moving object, and means for adjusting said plane on which said first and second images intersect to correspond with said three-dimensional position within said three-dimensional scene of said moving object.

Thus, the point of recreation of the images presented to the viewer occurs at the plane in the scene which corresponds to the three-dimensional position within the scene of the moving object (e.g. a surgeon's instrument) on which the viewer's eyes will be focused.

Beneficially, the focus or display plane, on which a surrounding image is displayed is adjusted to correspond with the plane at which the first and second images intersect (i.e. the convergence plane).

The tracking means for tracking the position of the moving object may be extracted from three-dimensional ultrasound data by means of, for example, three-dimensional object recognition or by providing one or more ultrasound transducers for generating ultrasound signals at known positions on said object. The three-dimensional scene beneficially comprises ultrasound data. However, it will be appreciated that the present invention may be applied to other modalities that can deliver real-time three-dimensional data for use in processes such as surgical interventions. At present, as well as ultrasound, these modalities could include stereo X-ray display systems and MRI.

The plane on which the first and second images intersect (or the perceived depth of the resultant reconstructed image seen by the viewer) is beneficially dynamically adjusted to correspond with the tracked position of the moving object within the scene, preferably by adjusting the x-axis separation between the first and second images. The three-dimensional scene may be displayed for use during a guided intravention using a surgical instrument, wherein the three-dimensional position of the surgical instrument within the displayed three-dimensional scene of a part of a subject's anatomy is tracked and the plane at which the first and second images intersect is dynamically adjusted accordingly.

The present invention extends to a method of displaying a three-dimensional scene during an intervenous procedure using a surgical instrument, the method comprising presenting first and second images to a viewer's left and right eyes respectively, said first and second images comprising first and second perspectives of a three-dimensional scene to be displayed, said first and second images intersecting at a point of recreation on a plane of said three-dimensional scene, tracking the three-dimensional position within said three-dimensional scene of said surgical instrument, and adjusting said plane on which said first and second images intersect to correspond with said three-dimesnional position within said three-dimensional scene of said surgical instrument.

These and other aspects of the invention will be apparent from and will be elucidated with reference to the embodiments described hereinafter.

BRIEF DESCRIPTION OF THE DRAWINGS

The present invention will now be described in more detail, by way of example, with reference to the accompanying drawings, wherein.

DETAILED DESCRIPTION OF THE INVENTION

Figure 1:
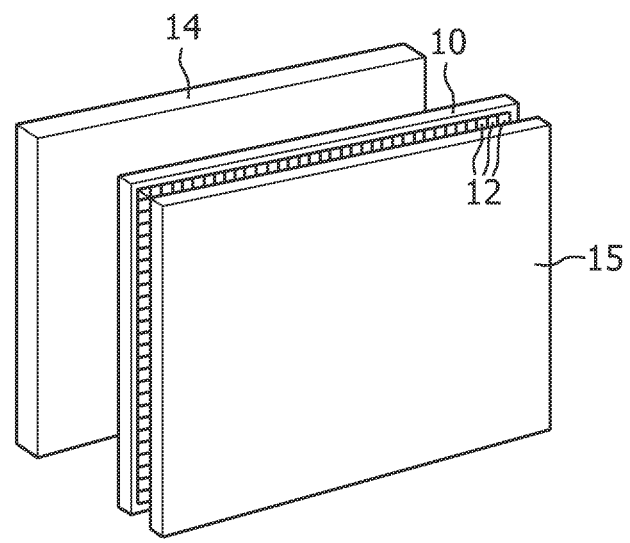
FIG. 1 is a schematic perspective view of an autostereoscopic display apparatus.
Figure 2:
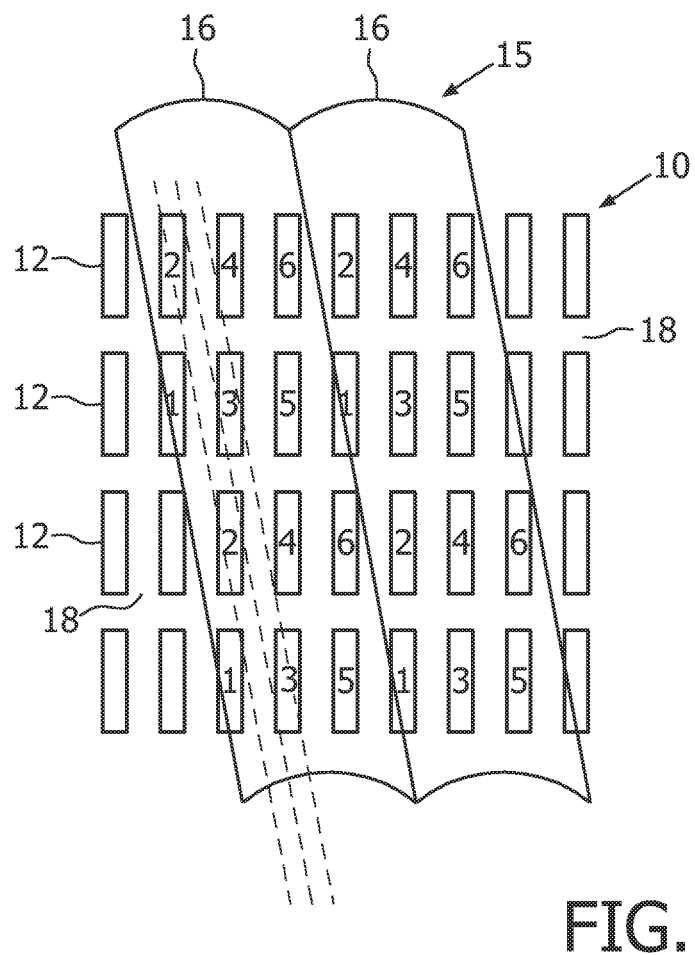
FIG. 2 is a schematic plan view of a part of the display element array of the display panel of FIG. 1, providing a six view output.
Figure 3:
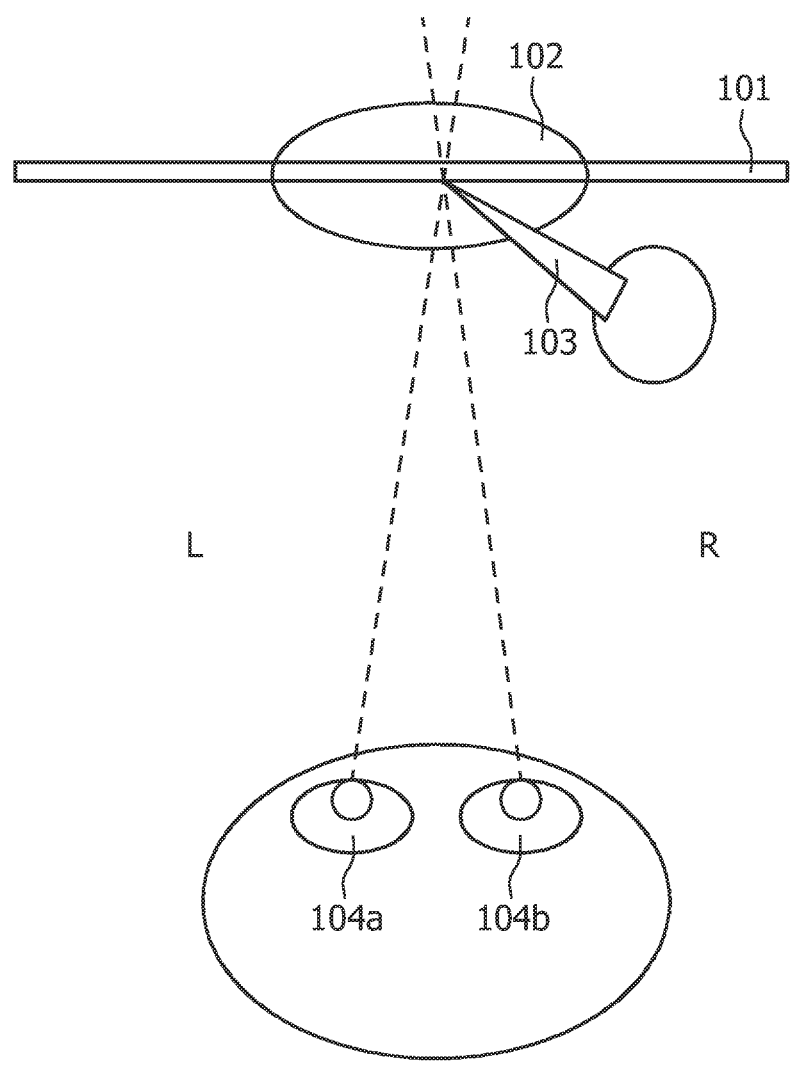
FIG. 3 is a schematic illustration of the principle of an autostereoscopic display system according to an exemplary embodiment of the present invention.

An example of a direct-view (autostereoscopic) type of display apparatus will now be described with reference to FIGS. 2 and 3 of the drawings, although a more detailed description of this apparatus is given in EP-A-0791847. It will be appreciated that FIGS. 2 and 3 are merely schematic and are not drawn to scale. For clarity of illustration, certain dimensions may have been exaggerated whilst other dimensions may have been reduced.

Referring to FIG. 2 of the drawings, the display apparatus includes a conventional liquid crystal display panel 10 used as a spatial light modulator and comprising a planar array of individually addressable and similarly sized display elements 12 arranged in aligned rows and columns perpendicularly to one another. Such panels are well known and will not, therefore, be described herein in detail.

The display elements 12 are substantially rectangular in shape and are regularly spaced from one another with the display elements in two adjacent columns being separated by a gap extending in column (vertical) direction and with the display elements in two adjacent rows being separated by a gap extending in the row (horizontal) direction. The panel 10 is of the active matrix type in which each display element is associated with a switching element, comprising for example a TFT or thin film diode situated adjacent the display element.

The display panel 10 is illuminated by a light source 14 which, in this example, comprises a planar back-light extending over the area of the display element array. Light from the source 14 is directed through the panel with the individual display elements being driven, by appropriate application of drive voltages, to constituting the display produced thus corresponds with the display element array, each display element providing a respective display pixel.

Over the output side of the panel 10, opposite that facing the light source, there is disposed image deflection means in the form of a lenticular sheet 15 comprising an array of elongate, parallel lenticules 16 or lens elements, acting as optical director means to provide separate images to a viewer's eyes, producing a stereoscopic display to a viewer facing the side of the sheet 15 remote from the panel 10. The lenticules of the sheet 15, which is of conventional form, comprise convex cylindrical lenticules 16, or cylindrical graded refractive index cylindrical lenses. These lenses can also be realised from liquid crystal material, allowing the display to be switched between a conventional 2D mode as well as a 3D mode, as will be known to a person skilled in the art. Autostereoscopic display apparatus using such lenticular sheets in conjunction with matrix display panels are well known in the art although, unlike the conventional arrangement in such apparatuses, with lenticules extending parallel to the display pixel columns (corresponding to the display element columns), the lenticules in the apparatus of FIG. 2 are arranged slanted with respect to the columns of display pixels, that is, their main longitudinal axis is at an angle to the column direction of the display element array. This arrangement has been found to provide a number of benefits in terms of reduced resolution loss and enhanced masking of the black area between display elements, as is described in EP-A-0791847.

The pitch of the lenticules 16 is chosen in relation to the pitch of the display elements in the horizontal direction according to the number of views required, as will be described, and each lenticule, apart from those at the sides of the display element array, extends from top to bottom of the display element array. FIG. 3 illustrates an exemplary arrangement of the lenticules in combination with the display panel for a typical part of the display panel. The longitudinal axis of the lenticules, L, is slanted at an angle a to the column direction, C. In this example, the spacing between the longitudinal axes of the parallel lenticules is of such a width with respect to the pitch of the display elements in a row, and slanted at such an angle with respect to the columns of display elements, as to provide a six view system. The display elements 12 are numbered (1 to 6) according to the view-number to which they belong.

The individual, and substantially identical, lenticules of the lenticular sheet 15, here referenced at 16, each have a width which corresponds approximately to three adjacent display elements (sub-pieces) in a row, i.e. the width of three display elements and three intervening gaps. Display elements of the six views are thus situated in groups comprising display elements from two adjacent rows, with three elements in each row.

The individually operable display elements are driven by the application of display information in such a manner that a narrow slice of the 2D image is displayed by selected display elements under a lenticule. The display produced by the panel comprises six interleaved 2D sub-images constituted by the outputs from respective display elements. Each lenticule 16 provides six output beams from the underlying display elements with view-numbers 1 to 6 respectively whose optical axes are in mutually different directions and angularly spread around the longitudinal axis of the lenticule. With the appropriate 2D image information applied to the display elements and with a viewer's eyes being at the appropriate distance to receive different onesd of the output beams then a 3D image is perceived. As the viewer's head moves in the horizontal (row) direction then a number of stereoscopic images can be viewed in succession. Thus, a viewer's two eyes would see respectively, for example, an image composed of all display elements "1" and an image composed of all display elements "2". As the viewer's head moves, images comprised of all display elements "2" and all display elements "3" will be seen by respective eyes, then images comprised of all display elements "3" and all display elements "4", and so on.

An exemplary embodiment of an autostereoscopic display is described in detail above, but it will be appreciated that many different types of autostereoscopic display are known, and the present invention is not intended to limited in this regard.

Referring to FIG. 3 of the drawings, and as explained above, during a medical intervention, such as ultrasound-guided interventions, a surgeon would be watching three-dimensional ultrasound data 102, rendered for at least two views, on an autostereoscopic display panel 101 which provides a depth sensation by providing the viewer's left and right eyes 104a, 104b with different images. It is advantageous to align the above-mentioned point of recreation of those images, i.e. the plane where the two (or more) views intersect, with the plane on which the surgeon's eyes are focused. During a medical intervention, this will tend to be the plane in which the instrument 103 being manipulated is located.

Thus, the object of the present invention can be achieved by controlling the perceived depth of the of the image presented to the viewer by adjusting the plane where the left and right images L, R intersect to correspond exactly with the position of the instrument 103 being used by the surgeon. The perceived depth of the image is controlled by the amount of x-axis separation of the two images L,R. The greater the x-axis separation of the images L, R the more depth there is in the resulting stereoscopic image.

The three-dimensional position of the instrument 103 can be extracted from the three-dimensional ultrasound data by means of one or more known techniques, for example, three-dimensional object recognition or by means of providing the instrument or tool 103 with one or more transducers which emit ultrasonic signals at known positions on the tool 103. In U.S. Pat. No. 6,246,898 there is described a surgical instrument with multiple ultrasound transducers for tracking and imaging the instrument. However, many different tracking techniques are envisaged to track the three-dimensional position of the instrument 103, and the present invention is not intended to be limited in this regard.

Thus, as the position of the tool is tracked, the plane of intersection of the stereoscopic image pairs L, R presented to the viewer is adjusted dynamically to correspond exactly therewith by adjusting the x-axis separation between the two images L, R.

Figure 4:
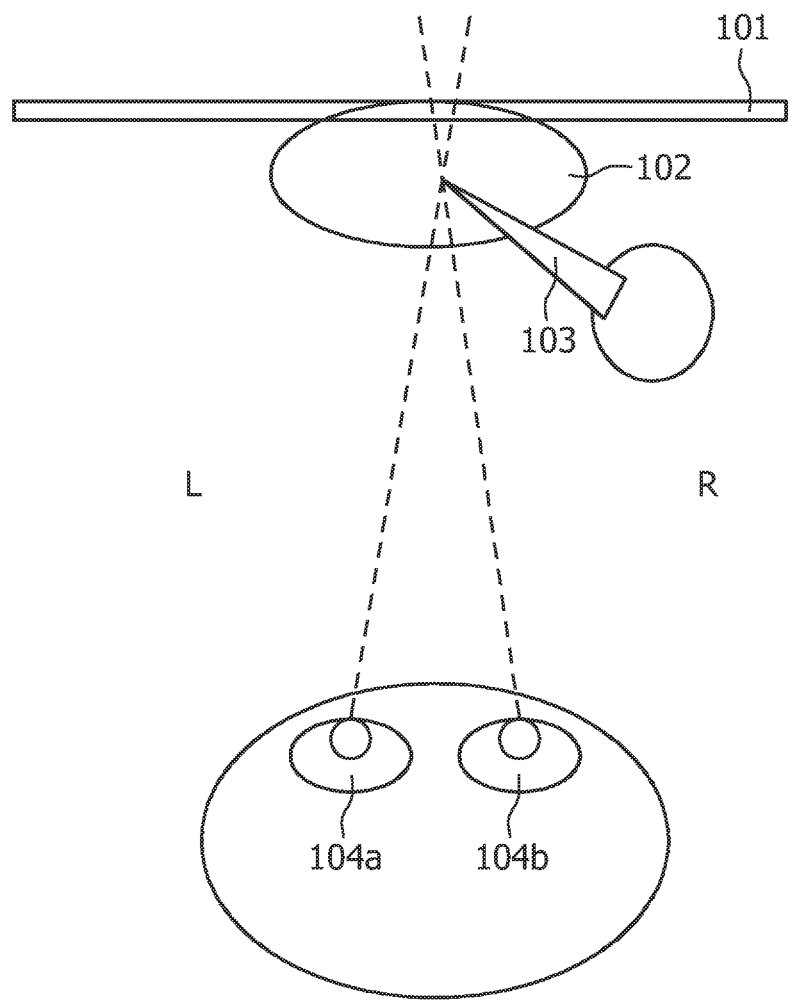
FIG. 4 is a schematic illustration of an autostereoscopic display system in which the three-dimensional location of the surgical instrument does not correspond with the display plane.
Figure 5:
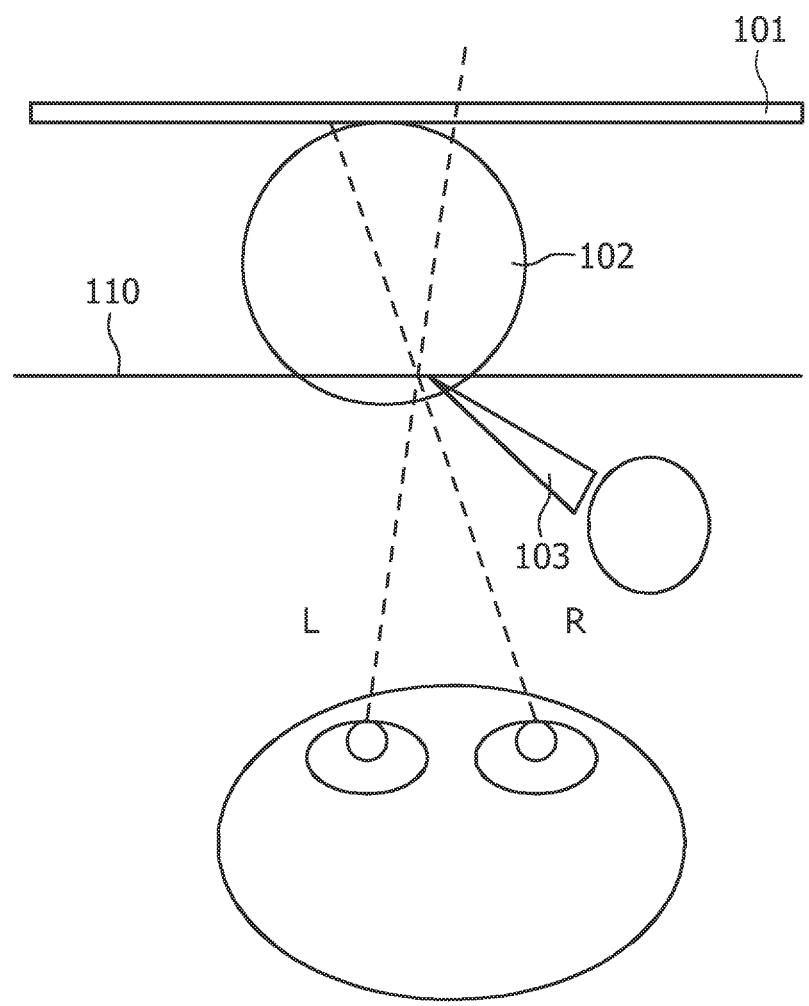
FIG. 5 illustrates schematically the effect when the convergence plane and focus plane in an autostereoscopic display system do not correspond.

In the example illustrated with reference to FIG. 3, the convergence plane, which corresponds with the plane in which the instrument 103 is located, corresponds with the display plane 101. In the event that the convergence plane (where the images L, R intersect) does not correspond with the display plane 101, as illustrated in FIG. 4 of the drawings, there are a number of disadvantages. Referring to FIG. 5 of the drawings, in the event that the convergence plane 110 (where the images L, R intersect) does not correspond with the focus plane (which corresponds to display plane 101), the viewer may experience eye strain characterized by headaches. Furthermore, pixels are at their sharpest at the display plane 101, so if the convergence plane 110 (where the viewer's eyes are focused) and the display plane 101 correspond, then image sharpness is optimised. Thus, for example, if the instrument 103 is moved toward the viewer (in three dimensions), the display plane (101) is preferably moved backward, and vice versa.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. An autostereoscopic display system comprising means for presenting first and second images to a viewer's left and right eyes respectively, said first and second images comprising first and second perspectives of a three-dimensional scene to be displayed, said first and second images intersecting at a point of recreation on a plane of said three dimensional scene, the system further comprising a tracking device for determining the three-dimensional position within said three-dimensional scene of a moving object, and wherein the autostereoscopic display system adjusts said plane on which said first and second images intersect to correspond with said three-dimensional position within said three-dimensional scene of said moving object,
wherein the means for presenting first and second images to the viewer's left and right eyes respectively comprises:
a display panel having a plurality of display elements arranged in a matrix of rows each extending in a row direction and columns each extending in a column direction perpendicular to the row direction, the display panel displaying the first and second images; and
a lenticular sheet disposed above the display panel, wherein the lenticular sheet comprises an array of elongate parallel lenticules acting as an optical director to direct the first and second images to the viewer's left and right eyes respectively, wherein the lenticules are slanted at an angle with respect to the columns of the display element.

2. The autostereoscopic display system of claim 1, wherein the plane on which a surrounding image is displayed is adjusted to correspond with the plane at which said first and second images intersect.

3. The autostereoscopic display system of claim 1, wherein the tracking device is arranged to extract data representative of said position of said moving object from three-dimensional image data generated by irradiating a subject to be imaged with radiation and detecting the intensity distribution of the radiation that has been transmitted through said subject.

4. The autostereoscopic display system of claim 3, wherein said tracking device is arranged to extract data representative of said position of said moving object from said three-dimensional image data by three-dimensional object recognition or by providing one or more ultrasonic transducers for generating ultrasound signals at known positions on said moving object.

5. The autostereoscopic display system of claim 3, wherein said image data comprises ultrasound image data.

6. The autostereoscopic display system of claim 1, wherein the plane on which the first and second images intersect is dynamically adjusted to correspond with the tracked position of the moving object within the scene by adjusting the x-axis separation between the first and second images.

7. The autostereoscopic display system of claim 1, wherein the three-dimensional scene is displayed for use during a guided intravention using a surgical instrument, wherein the three-dimensional position of the surgical instrument within the displayed three-dimensional scene of a part of a subject's anatomy is tracked and the plane at which the first and second images intersect is dynamically adjusted accordingly.

8. The autostereoscopic display system of claim 1, wherein the tracking device is arranged to extract data representative of said position of said moving object from said three-dimensional image data by three-dimensional object recognition.

9. A method of displaying a three-dimensional scene during an intravenous procedure using a surgical instrument, the method comprising presenting first and second images to a viewer's left and right eyes respectively, said first and second images comprising first and second perspectives of a three-dimensional scene to be displayed, said first and second images intersecting at a point of recreation on a plane of said three-dimensional scene, tracking the three-dimensional position within said three-dimensional scene of said surgical instrument, and adjusting said plane on which said first and second images intersect to correspond with said three-dimensional position within said three-dimensional scene of said surgical instrument,
wherein presenting first and second images to a viewer's left and right eyes respectively, comprises:
displaying the first and second images on a display panel having a plurality of display elements arranged in a matrix of rows each extending in a row direction and columns each extending in a column direction perpendicular to the row direction; and
directing the first and second images to the viewer's left and right eyes by a lenticular sheet disposed above the display panel, wherein the lenticular sheet comprises an array of elongate parallel lenticules slanted at an angle with respect to the columns of the display elements.

10. The autostereoscopic display system of claim 1, wherein each lenticule has a width approximately equal to three columns of the display elements.

11. The autostereoscopic display system of claim 1, wherein the display panel displays six images, and the lenticular sheet directs two of the six displayed images to the viewer's left and right eyes to be the first and second images, wherein the two images that are directed to be the first and second images among the six displayed images changes as the viewer moves the left and right eyes in the row direction.

12. The method of claim 9, further comprising adjusting a plane on which a surrounding image is displayed to correspond with the plane at which said first and second images intersect.

13. The method of claim 9, wherein the display panel displays six images, and the lenticular sheet directs two of the six displayed images to the viewer's left and right eyes to be the first and second images, wherein the two images that are directed to be the first and second images among the six displayed images changes as the viewer moves the left and right eyes in the row direction.

* * * * *